United States Patent [19]

Smith et al.

[11] 4,002,061
[45] Jan. 11, 1977

[54] CAPACITANCE TRANSDUCER FOR THE MEASUREMENT OF BENDING STRAINS AT ELEVATED TEMPERATURES

[75] Inventors: Hugh H. Smith, Oxon Hill, Md.; David J. Michel; Paul Shahinian, both of Alexandria, Va.

[73] Assignee: The United States of America as represented by the Secretary of the Navy, Washington, D.C.

[22] Filed: Apr. 30, 1976

[21] Appl. No.: 681,964

[52] U.S. Cl. .......................... 73/88.5 R; 73/141 A
[51] Int. Cl.² ......................................... G01N 3/20
[58] Field of Search ............... 73/88.5 R, 141 A, 89

[56] References Cited
UNITED STATES PATENTS

| | | | |
|---|---|---|---|
| 3,602,866 | 8/1971 | Saxl | 73/88.5 R |
| 3,729,985 | 5/1973 | Sikorra | 73/88.5 R |

*Primary Examiner*—James J. Gill
*Assistant Examiner*—Anthony V. Ciarlante
*Attorney, Agent, or Firm*—R. S. Sciascia; Philip Schneider; Melvin L. Crane

[57] ABSTRACT

A capacitance-type transducer used for the measurement of bending strains in test elements which are not sufficiently strong to support a strain element or for test elements in which a strain element would strengthen the test element and not give an accurate test. The transducer is formed by a spring wire which has a portion perpendicular to the test specimen with a U-shaped end extending from the perpendicular portion. One portion of the U-bend has an insulator about the wire where the insulator parallels the test specimen surface and is in contact therewith. The end of the wire has a flat conductive plate secured thereto with the flat plate parallel with the specimen. The spacing between the flat plate and the specimen forms the capacitance spacing which changes as the specimen is strained in a direction perpendicular to the flat plate. The distance between the flat plate and specimen is represented by a change in capacitance which is measured by an oscilloscope. The change in capacitance is used to calibrate the strain on the specimen.

3 Claims, 3 Drawing Figures

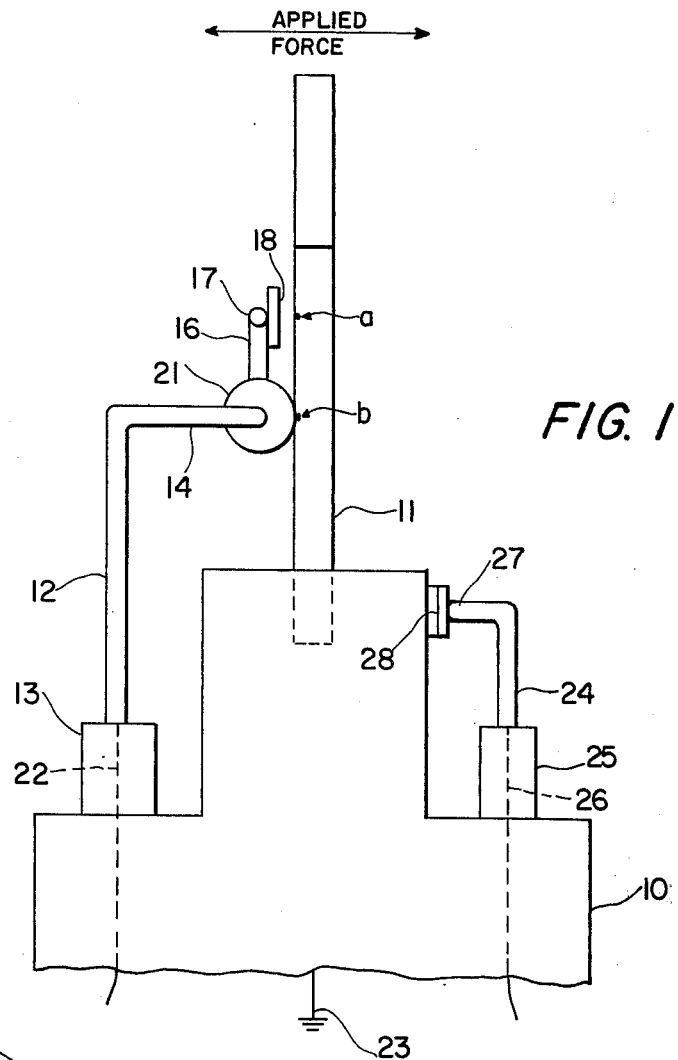
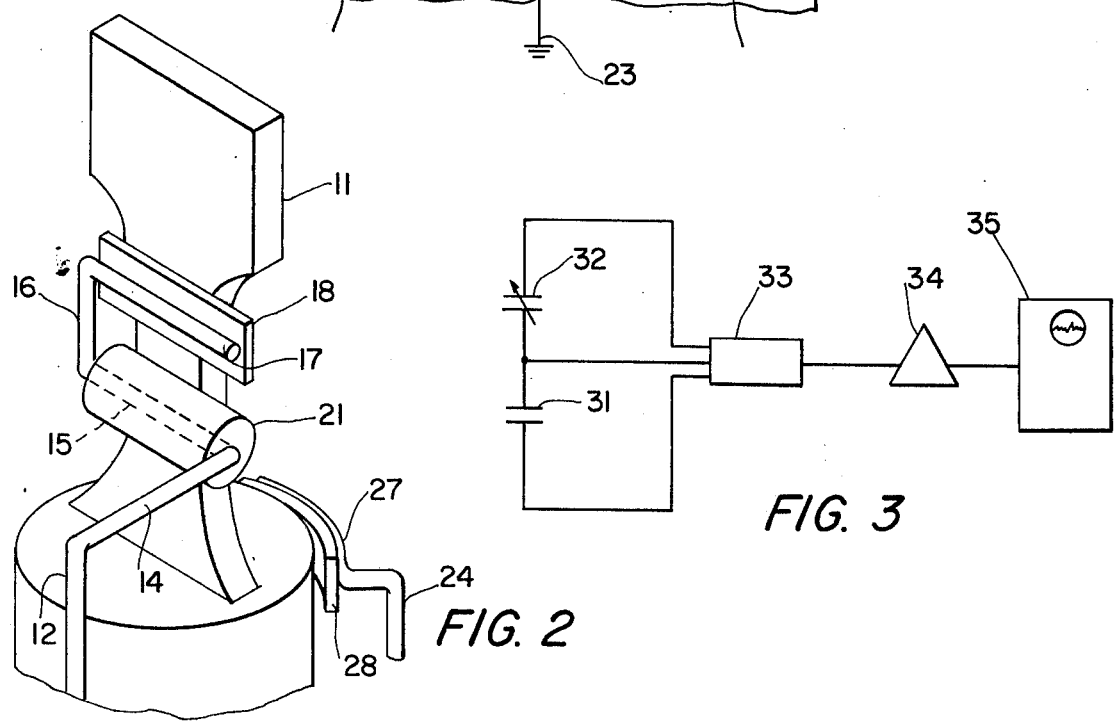

CAPACITANCE TRANSDUCER FOR THE MEASUREMENT OF BENDING STRAINS AT ELEVATED TEMPERATURES

BACKGROUND OF THE INVENTION

The invention relates to a system for measuring strain on thin flexible specimens and more particular to a system for measuring strain of such specimen without the application of a strain element onto the specimen.

Heretofore strain has been determined on some elements by resistance elements attached to the surface of the element to be tested. Other methods include fatigue machines, as well as optical systems. Such systems have been set forth in an article, "Flexural Fatigue Machine for High Temperature Operation At Resonance in Vacuum" by Achter et al, *Review of Scientific Instruments*, No. 37, page 311, March 1966; and an article "An Optical Technique for the Measurement of Plastic Bending Strains at Elevated Temperature," by Danek et al, *NRL Report* 5661, August 1961, published by the Naval Research Laboratory, Washington, D.C. 20375. When some types of strain gages are applied to thin elements, the strain gages strengthen the test sample therefore a true test is not obtained.

In carrying out some research, it is necessary that the test be carried out in a vacuum, at high temperatures, and sometimes require remote operation because of radioactive materials. Prior art strain test devices are not suitable for all of the above; therefore a new system has been developed which is suitable for the above situations.

SUMMARY OF THE INVENTION

This invention provides a system which is useful at high temperatures; it will not affect the characteristics of the test specimen and can be remotely operated. No strain elements are secured to the test specimen and the parts in the system are either metal, ceramic or quartz which will withstand high temperatures.

BRIEF DESCRIPTION OF THE DRAWING

FIG. 1 is a side view which illustrates the relative parts.

FIG. 2 is a perspective view which shows more detail of the elements.

FIG. 3 illustrates a simplified block diagram of the electrical system for measuring the strain of a test specimen.

DETAILED DESCRIPTION

Now referring to the drawing, there is shown for illustrative purposes a capacitance transducer-strain measuring device made in accordance with the teaching of this invention. The system includes a specimen holder 10 which secures a specimen 11 by one end in an upright position. A rigid, high-temperature-alloy electrically conductive, spring-type wire 12 is secured at one end by a ceramic binding post 13 or any other similar insulator which is supported by the specimen holder. The conductive wire extends upwardly parallel with the specimen and is bent at a 90° angle so that a portion 14 is directed toward and perpendicular with the specimen. The conductive wire is bent again at an angle of 90° along the width of the specimen to provide a portion 15 which is parallel with the specimen and extending in a horizontal direction. The conductive wire is bent upwardly at another 90° angle so that the portion 16 is parallel with the specimen. The conductive wire is bent again at another 90° angle along the width of the specimen so that the end portion 17 is on a horizontal line parallel with the specimen and also parallel with the portion 15 and in the same plane. The portions 15, 16 and 17 form a U-shape which is parallel with the specimen. A metal plate 18 is spot-welded to the end 17 so that the metal plate is spaced from the specimen and extends across the width of the specimen with one face parallel with the specimen. The conductive wire portion 15 is surrounded by a cylindrical quartz insulator 21 which rests against the face of the specimen in the test area. The bottom of the metal plate on the upper end of the wire is parallel with the quartz insulator and the face of the plate is spaced from the face of the specimen. The conductive wire 12 has an electrical conductor 22 connected thereto at its supported end which connects the conductive wire 12 to an electrical circuit. The specimen is grounded at 23 so that a capacitor is formed by the metal plate 18 and the specimen opposite the metal plate. As the specimen is flexed by an applied force, a change in capacitance is made due to movement of the specimen in relationship to the plate 18.

The system is provided with a fixed capacitor in order to provide a null in the output. Therefore a conductor wire 24 which may be a high-temperature-alloy, spring-wire is secured at one end by a ceramic binding post 25 and connected to an electrical wire 25 that connects into the electrical circuitry. The opposite end 27 of the conductive wire 24 parallels the face of the specimen pedestal and has a conductive plate 28 spot welded thereto. The end of the conductive wire and supported plate are secured such that they are adjacent to the pedestal so that the plate 28 forms a fixed capacitor.

FIG. 3 illustrates a simplified block diagram of the electrical components of the electrical system for the capacitance transducer system. As shown, the system includes a fixed capacitor 31 formed by the pedestal specimen 23 and the fixed plate 28 and a variable capacitor 32 formed by plate 18 and the movable specimen portion 11. The outputs or changes in capacitance of the capacitors are directed into a probe 33 such as a General Purpose Probe, Model GP 311, manufactured by Lion Research Corp. of Newton, Mass. The probe converts the capacitance changes into a dc analog signal which is directed to a differential amplifier 34 whose output is measured by any suitable equipment or displayed by any dynamic recording device such as an oscilloscope 35. The probe, differential amplifier, and oscilloscope forms no part of this invention and can be any suitable equipment for measuring and displaying the capacitance changes. Such systems are well known in the strain gage art.

In construction and operation, the fixed capacitor plate 28 is placed parallel with the specimen pedestal at a point near the secured end of the specimen. Thus, a fixed capacitor is formed. The quartz insulator on portion 15 of the electrical conductor 12 rests against the specimen at point *b*. The conductor is made of spring-wire material and positioned such that the quartz insulator is always in contact with the specimen at point *b*, even when a force is applied to the upper end of the specimen to produce reverse bending. As the specimen is cycled, the distance between the specimen and the plate 18, at point *a*, alternately increases and decreases causing a corresponding decrease and increase in capacitance between the plate 18 and the specimen at point $a$. Meanwhile, the spacing between the specimen pedestal and plate 28 remains the same therefore the capacitance output for the fixed capacitor remains constant. The change in capacitance is converted into an analog voltage by suitable equipment as set forth above. The transducer or variable capacitor measures the movement of point $a$ with respect to point $b$ of the test specimen. Even though the specimen is strained along its length, the transducer only measures the deflection in the section of the specimen between points $a$ and $b$.

In order to calibrate the transducer system, room temperature measurements are made on a similar material and type test specimen to which a conventional thin foil type gage has been attached. Knowing the relationship between strain and capacitance transducer output, strain measurements can be then made in vacuum or in environments at high temperatures.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A capacitance transducer for the measurement of bending strains of a test specimen which comprises:
   means for supporting said test specimen in a vertical plane;
   a high-temperature-alloy, electrical conductor spring wire supported at one end and having a U-shaped portion at the unsupported end with the U in a vertical plane parallel with the plane in which said specimen is supported;
   a high-temperature-type insulator surrounding the inner electrical leg portion of said U-shaped end and adapted to be in contact with said test specimen;
   a metal plate secured to and along the outer leg of said U-shaped portion of said wire conductor with said metal plate extending in a vertical plane parallel with the vertical plane of said U-shaped end and said specimen;
   a second high-temperature-alloy, spring-wire, electrical conductor supported at one end with its unsupported end adjacent said test specimen supporting means and near the supported end of said specimen;
   a flat metal plate secured to and along said unsupported end of said second electrically conductive wire parallel to said test specimen supporting means;
   whereby the deflection of said specimen is determined by changes in capacitance between said metal plate on said U-shaped end of said conductive wire and said specimen and said deflection is calibrated into strain.

2. A capacitance transducer as claimed in claim 1 where:
   said high-temperature-alloy, spring-wire, electrical conductors are secured in a ceramic binding post.

3. A capacitance transducer as claimed in claim 2 wherein:
   said high-temperature electrical insulation on said U-shaped portion of said conductor is quartz.

* * * * *